United States Patent [19]

Nagasawa et al.

[11] Patent Number: 4,605,614
[45] Date of Patent: Aug. 12, 1986

[54] METHOD FOR MEASURING PLASMIN

[75] Inventors: Takeshi Nagasawa; Katsumasa Kuroiwa; Katsuyuki Takabayashi; Yoshio Nakamura, all of Koriyama, Japan

[73] Assignee: Nitto Boseki Co., Ltd., Fukushima, Japan

[21] Appl. No.: 579,868

[22] Filed: Feb. 13, 1984

Related U.S. Application Data

[62] Division of Ser. No. 417,377, Sep. 13, 1982, Pat. No. 4,452,736.

[30] Foreign Application Priority Data

Oct. 14, 1981 [JP] Japan .................. 56-163649

[51] Int. Cl.$^4$ .................. C12Q 1/56; C12Q 1/38
[52] U.S. Cl. .................. 435/13; 435/23
[58] Field of Search .................. 435/4, 13, 23, 24

[56] References Cited

U.S. PATENT DOCUMENTS

| 3,886,136 | 5/1975 | Claeson et al. | 435/13 |
| 3,886,896 | 5/1975 | Blomback | 435/13 |
| 4,257,940 | 3/1981 | Fujii et al. | 435/24 |

Primary Examiner—Esther M. Kepplinger
Attorney, Agent, or Firm—Bert J. Lewen; Henry Sternberg

[57] ABSTRACT

A method for measuring the activity of plasmin in plasma which comprises reacting a compound of the following formula or a salt thereof;

$$D\text{-}H_2N\text{-}CH\text{-}CNH\text{-}CH\text{-}C\text{-}CH\text{-}C\text{-}NH\text{-}C$$

with substituents $(CH_2)_m$, $A$, $B$, $(CH_2)_4$, $NH_2$ wherein
$m = 1, 2, 3$ or $4$ $$A = -CNHR_1, -COR_1, -NHCR_2 \text{ or } -NHSO_2R_2$$

$B = -CH_2CH(CH_3)_2$ or $-CH_2-\phi$ $C = -\phi-NO_2$, or $-\phi(OH)(COOH)$ wherein $R_1 = -(CH_2)_{n+1}-\phi R_3$ ($n = 0, 1, 2$ or $3$, $R_3 = H$ or $CH_3$), $-(CH_2)_n-CH(CH_3)_2$ ($n = 0, 1, 2$ or $3$)

cyclohexyl (H)

$R_2 = -(CH_2)_{n+1}-CH_3$ ($n = 0, 1, 2$ or $3$)

$-(CH_2)_n-\phi(R_4, R'_4, R''_4)$ ($n = 0, 1, 2$ or $3$, $R_4$, $R'_4$ and $R''_4$ are H or $CH_3$), naphthyl or methylnaphthyl with plasmin in a buffer solution having a pH of 7.2 to 7.6 and quantitatively determining the reaction product thereof.

2 Claims, No Drawings

METHOD FOR MEASURING PLASMIN

This is a division of application Ser. No. 417,377, filed Sept. 13, 1982, now U.S. Pat. No. 4,452,736.

The present invention relates to novel chromophoric and fluorescent substrates for plasmin and plasmin-like enzymes. The substrates of the present invention, as compared with the heretofore reported substrate, can quantitatively analyze plasmin with extremely good selectivity and with high sensitivity, and are especially suitable for researches on reactions in which plasmin is formed, inhibited or consumed, or measurements of factors relating thereto, for example, measurements of plasminogen, $\alpha_2$-PI (plasmin inhibitor) and plasmin.

The introduction of synthetic substrates in coagulation and linear dissolution reactions was started with the employment of ariginine esters such as TAMe (Tos-Arg-OMe) etc. synthesized by S. Sherry et al in 1954 [J.S.C., 208, 95–105 (1954)] in the measurement of the esterase activity of thrombin as the substrate, but there have been problems such as low specificity and sensitivity of the substrate since the ester melting activity did not correspond to the coagulation activity. However, thanks to the recent progress of peptide chemistry, a peptide substrate, Bz-Phe-Val-Arg-PNA (S-2160) resembling the amino acid structure of the part of fibrinogen cleaved by thrombin was synthesized by Blömback et al [Thromb. Research 1 267–278 (1972)], and this has gradually become to be used in researches and testings, because the enzymatic chemical spectroscopy based on the yellow color development of paranitroaniline (PAN) which has been liberated by having undergone the enzymatic reaction is easy, the preparation of the reagents is easy and so forth. Further, as substrate for plasmin, Tos-Gly-Pro-Lys-PNA (CHR-PL, Pentapharm Co.) [Japanese Patent Application Laid-open No. 52-3494] and H-D-Val-Leu-Lys-PNA (S-2251, Kabi Co.) [Japanese Patent Application Laid-open No. 52-24581] have been successively developed, and thereafter a fluorescent peptide substrate to which aminomethylcoumarin (AMS) similarly emitting fluorescence when liberated had been attached was also developed by Iwanaga et al (1977) [J. Biochem., 82 1495–1498 (1977)].

On the other hand, it is important for the synthetic substrates for measuring enzymes to satisfy four points namely, high sensitivity and specificity for the enzyme, good solubility in aqueous or biological testing solutions and easy detectability of the decomposition product.

Among the above, the high specificity and reactivity for the enzyme to be measured is of a particular importance.

On the other hand, the reactivity of the substrates heretofore developed for plasmin towards enzymes is relatively low as compared with that of those for thrombin. For example when Michaelis's constants (Km), each of which is the index for the reactivity between the enzyme and the substrate are compared, there is a difference of more than one order, that is, $3 \times 10^{-4}$ mole/l in the case of S-2251 (Human Plasmin) and $0.7 \times 10^{-5}$ mole/l in the case of S-2238 (Human Thrombin). In order to lessen the influence by the change in concentration of the substrate due to the reaction, for actually employing in measurements, it is generally necessary to make the substrate concentration in the reaction system considerably greater than the Km value (desirably 5 Km or higher), but if the Km value itself is great, it is then difficult to avoid the influence by the change in concentration of the substrate and therefore the development of a substrate having a smaller Km value has been desired.

In general, when plasmin, plasminogen or the like is to be measured utilizing chromophoric substrate, if it undergoes a cross reaction with thrombin, FXa, urokinase (UK) etc. which are coagulation and linear dissolution related enzymes other than plasmin and are presumably present in the plasma, accurate measurement can not be expected.

As the best substrates for plasmin ever developed, the above-described CHR-PL and S-2251 may be mentioned, but they are not entirely satisfactory from the view of their substrate specificity and reactivity.

In other words, for instance, CHR-PL, although having a Km value smaller than that of S-2251, considerably reacts with coagulation and linear dissolution related enzymes such as thrombin, Factor Xa, UK etc., and even in the case of S-2251 which is said to have comparatively good selectivity, the reactivity (Km and Vmax/Km) is not entirely satisfactory.

In order to improve the above points, the present inventors have been intensively studying on the amino acid arrangements, chromophoric groups, protecting groups for the amino acids, etc. for the substrates for plasmin so that the following points:

(1) the reactivity is good (Km is small, Vmax is great and Vmax/Km is small), (2) the selectivity is good (the cross reaction rarely occurs)

(3) the solubility is good, (4) the detecting method is easy and the highly sensitive color development is permitted without influences by the plasma components, and so forth are satisfied, and as the result, have discovered that the reactivity with plasmin can be greatly improved by reacting the functional group of the amino acid side-chain of the N-terminal of the substrate (e.g. in the case of lysine, $\omega$-amino group) with other compound (e.g. tosyl chloride) to extend the chain length.

For instance, in the case of NPN-2H-D-Lys-(Tos)-Phe-Lys-PNA which is one of the compounds of the present application, its reactivity with Porcine Plasmin (pig plasmin) is compared with those of CHR-PL and S-2251 as shown below.

| (Compound of the Present Application) | Km ($\times 10^{-5}$) [mole/l] | Vmax ($\times 10^{-6}$) [mole/min/Cu] | $V/K_m$ ($\times 10^{-3}$) |
|---|---|---|---|
| NPN-2 | 1.6 | 4.8 | 303.6 |
| CHR-PL | 27.8 | 6.0 | 21.6 |
| S-2251 | 34.8 | 4.0 | 11.4 |

The synthesis of the substrates for measuring plasmin having both KM and V/Km remarkably improved has now thus been succeeded. In other words, as compared with S-2251, the Km value is actually 1/22, the Vmax is 1.2 times and the V/Km value which is the index for the reactivity is 26.7 times, and thus it can be seen that the present substrate is very superior as compared with the conventional ones.

Similarly, when the effects by the amino acid arrangements were examined by changing the chromophoric group to 3-carboxy-4-hydroxyanilide, as shown in Table 2 of Example 3, it has also been found that the amino acid arrangement of the present invention is remarkably improved as compared with the conventional amino acid arrangement, H-D-Val-Leu-Lys-CHA.

The novel chromophoric or fluorescent substrates by the present invention are compounds of the following general formula or salts thereof:

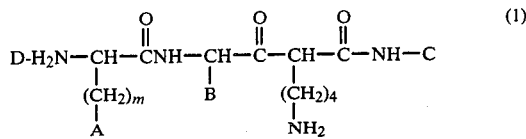

wherein m = 1, 2, 3 or 4

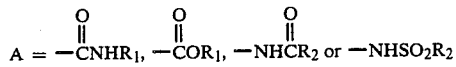

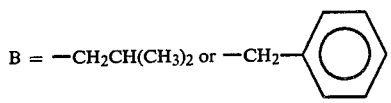

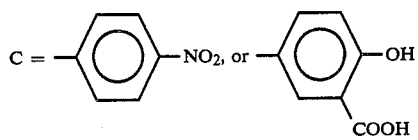

wherein

(n = 0, 1, 2 or 3, R₃ = H or CH₃)

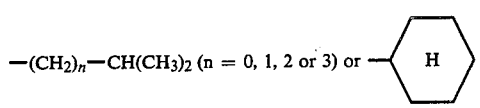 (n = 0, 1, 2 or 3) or 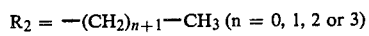

R₂ = —(CH₂)ₙ₊₁—CH₃ (n = 0, 1, 2 or 3)

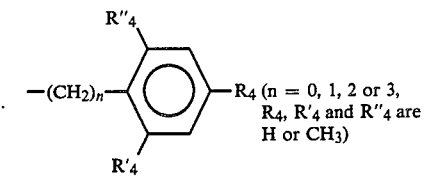
R₄ (n = 0, 1, 2 or 3, R₄, R'₄ and R''₄ are H or CH₃)

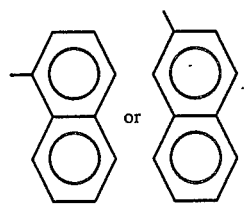

The applications of the compounds of the present invention are, as already described, as the substrates for measuring the plasmin activity. In this case, the plasmin activity is measured by reacting a substrate of the present invention with plasmin in a buffer solution having a pH of 7.2 to 7.6 to produce p-nitroaniline or 3-carboxy-4-hydroxy-aniline and then quantitatively determining those products (that is, p-nitroaniline is determined by itself at 405 nm, and 3-carboxy-4-hydroxyaniline is first oxidatively condensed with an appropriate coupler to convert to a colored substance and the substance is determined by colorimetry or fluorometry at 328 nm in the excited state or at 540 nm using fluorescence).

As the coupler, there may be employed anilinic compounds such as N,N-diethylaniline when the color is developed in the acidic side, and phenolic and naphtholic compounds such as 2,5-xylenol, 2,6-xylenol, 2,3-xylenol, thymol, o-cresol, o-ethylphenol, etc. when the color is developed in the alkaline side.

Further, as the oxidant for the oxidative condensation, while various agents such as hydrogen peroxide, persulfuric acid salts, etc. are employed, metaperiodic acid is suitable.

The dye produced by the oxidative condensation of 3-carboxy-4-hydroxyaniline and the above-described coupler has a maximum absorption wavelength widely distributed between 560–770 nm depending on the coupler but its fluctuation in color development with temperatures is very small and hence stable, thus this method is suitable for the measurement of the plasmin activity. Further, when the chromophoric sensitivities are compared, in the case of p-nitroaniline, absorbance is 10,600 at 405 nm which is a wavelength employed for general measurements, whereas in the color development using o-ethylphonol and 3-carboxy-4-hydroxyaniline, absorbance is 29,000 at $\lambda = 645$ nm and in the color development using 2,6-xylenol and 3-carboxy-4-hydroxyaniline, absorbance is 21,600 at $\lambda = 615$ nm; thus absorbance in the color development using 3-carboxy-4-hydroxyaniline is large and extremely advantageous in measurement. Further, since the substrates having 5-aminosalicyclic acid in the chromophoric group have hydrophilic functional groups, and the solubility in water is very good, and hence do not particularly need dissolving aids such as surfactants, organic solvents etc., they have advantages that they are very easily controlled in the reagent preparation or measuring operation and that the substrate concentration just necessary and satisfactory for the reaction can be employed.

As described above, it is evident that the compounds of the present invention are very excellent as the substrates for the plasmin activity as compared with the conventional products.

The compounds of the formula [I] of the present invention are synthesized by processes well known in peptide chemistry such as the process discribed in "Methoden der organische Chemie".

As the α-amino protecting group, it is advantageous to employ a carbobenzoxy or t-butyloxycarbonyl or related group, e.g. p-methoxy-p-nitro- or p-methoxyphenylazolcarbobenzoxy etc.

The coupling of the two amino acids or the coupling of the dipeptide and the amino acid may be effected by the activation of the α-carboxyl group. For instance, the reagent for activation of the α-carboxy group can be N-hydroxysuccinimide, p-nitrophenol, 4,6-dimethylpyrimidyl-2-thio etc. The activation to the above-described ester derivative is advantageously conducted in the presence of a carbodiimide, for example, N,N-dicyclohexylcarbodiimide (DCC).

The substrate synthesis may be effected by attaching first the chromophoric group to the lysyl group and successively carrying out the couplings.

The present invention is now described in more detail by the following examples, but the present invention should in no way be restricted to these examples.

[1] Abbreviations
Gly=Glycine

Glu=Glutamic acid
Leu=Leucine
Lys=Lysine
Phe=Phenylalanine
Pro=Proline
Thr=Threonine
Tyr=Tyrosine
Orn=Ornithine
Asp=Aspartic acid
Val=Valine
Z=Benzyloxycarbonyl
BOC=t-Butyloxycarboxyl
Z(OMe)=p-Methoxybenzyloxycarbonyl
Tos=p-Tolylsulfonyl
Mst=2,4,6-Trimethylbenzenesulfonyl
AC=Acetyl
NaC=β-Naphthylcarbonyl
NaS=β-Naphthylsulfonyl
DMF=Dimethylformamide
MeOH=Methanol
THF=Tetrahydrofuran
NEM=N-Ethylmorpholine
ESA=Ethanesulfonic acid
TEA=Triethylamine
TFA=Trifluoroacetic acid
DCHu=Dicyclohexylurea
Dcc=dicyclohexylcarbodiimide
-PNA=p-Nitroanilide
-CHA=3-Carboxy-4-hydroxyanilide
-SDP=4,6-Dimethylpyrimidin-2-thio
Bzl=Benzyl
TLC=Thin layer chromatography
GPC=Gel permeation chromatography
ToC=4-Methylbenzoyl
CHN=Cyclohexyl ester
AcOH=Acetic acid
AcOEt=Ethyl acetate

[2] Thin layer chromatography

For TLC analyses, silica gel $F_{254}$ (manufactured by Merck Co.) plates were employed, and the developing solvents were as follows:

$Rf_1$; $CHCl_3$:MeOH:ACOH:$H_2O$ = 80:20:25:5
$Rf_2$; n-BuOH:ACOH:$H_2O$ = 4:1:1
$Rf_3$; n-BuOH:ACOH:$H_2O$ = 4:1:5

[3] For gel permeation, hydroxypropylated cross-linked dextran gel Sephadex LH.-20 (trade name) manufactured by Pharmacia Fine Chemical Co. (Sweden) was employed.

EXAMPLE 1

Synthesis of 2HCl.H-D-Lys(ToS)-L-Phe-L-Lys-CHA (NPC-7)

I. HCl.H-Lys(Z)-CHA (m.w. 451.9) ((including BOC-Lys(z)-CHA))

70.4 g (0.14 mole) of BOC-L-Lys(Z)-SDP (m.w. 502.6) was dissolved in 200 ml of THF, which was then added dropwise to a solution of 21.4 g (0.14 mole) of 5-aminosalicylic acid (m.w. 153.14) in 187 ml of 1.5N NEM/DMF solution at 0°–5° C., and the reaction was effected at normal temperature for 18 hours, after which the reaction mixture was concentrated to 100–200 ml, 1600 ml of ether/ethyl acetate (50 v/50 v) was added, the mixture was washed with 1000 ml of cold 5% HCl three times and then with 1000 ml of saturated aqueous NaCl twice, active carbon was added, dried on magnesium sulfate, and the solvent was distilled off, to obtain, by recystallization from ether-/isopropyl ether, 8.9 g (yield 55%) of crystalline BOC-L-Lys(Z)-CHA (m.w. 515.6) of m.p. 102°–105° C.

Thereafter, 5.2 g (0.01 mole) of the BOC-L-Lys(Z)-CHA (m.w. 515.6) was dissolved in 25 ml (0.05 mole) of 2N HCl/acetic acid to effect the liberation of the BOD. After reacting for 2 hours, 1 liter of ether was added to the reaction mixture to precipitate crystals, which were filtered out and dried.

II. BOC-L-Phe-L-Lys(Z)-CHA (m.w. 662.74)

63.3 g (0.14 mole) of HCl-H-L-Lys(Z)-CHA (m.w. 451.9) was dissolved in 280 ml of 1.5N NEM/DMF, and to this solution was added dropwise a solution of 54.3 g (0.14 mole) of BOC-Phe-SDP (m.w. 387.504) in 200 ml of DMF at 0°–5° C.

After reacting overnight, the DMF was distilled off, 1000 ml of AcOEt was added, the mixture was washed with 1000 ml of cold 5% HCl twice and then with 500 ml of saturated aqueous NaCl, after which it was dried on magnesium sulfate, the AcOEt was distilled off, and the residue was recrystallized from ethyl acetate/n-hexane to obtain 61.2 g (yield 66%) of crystals of BOC-L-Phe-Lys(Z)-CHA.

m.p.: 151°–155° C.
[α]: −5.7 (Cl. DMF).

III. HCl.H-Phe-Lys(Z)-CHA (m.w. 599.1)

250 ml of 1.5N HCl/acetic acid was added to 60.2 g (0.0908 mole) of the BOC-Phe-Lys(Z)-CHA (m.w. 662.747), and the reaction was effected at normal temperature. The precipitated crystals were filtered out and dried.

Yield: 49.9 g (89.1%).
m.p.: 222°–230° C.
[α]: −12.3 (Cl. MeOH).
$Rf_1$: 0.17.

IV. Z-D-Lys(Tos)-Phe-Lys(Z)-CHA (m.w. 979.1)

13.5 g (0.0225 mole) of the HCl.H-Phe-Lys(Z)-CHA (m.w. 599.1) was dissolved in 45 ml of DMF, to which was added dropwise a solution of 12.5 g (0.0225 mole) of Z-D-Lys(Tos)-SDP (m.w. 556.708) in 45 ml of DMF at 0°–5° C. and the reaction was effected overnight, after which 1500 ml of ethyl acetate was added, the mixture was washed with 800 ml of cold 5% HCl twice and then with 600 ml of saturated aqueous NaCl, dried, concentrated and recrystallized from MeOH to obtain 12.9 g (58.6%).

m.p.: 188°–195° C.
[α]: −8.9 (Cl. DMF).
$Rf_1$: 0.49.

V. 2HCl.H-D-Lys-(Tos)-L-Phe-L-Lys-CHA (m.w. 783.8)

1.96 g (2 mmole) of Z-D-Lys(ToS)-L-Phe-L-Lys(-ToS)-CHA (m.w. 979.128) was dissolved in 5 ml of 5% HCl-MeOH and 120 ml of MeOH, 1 g of Pd/C was added, and the catalytic reduction was effected for 4 hours. After completion of the reaction, the MeOH was distilled off, the residue was treated with ether to crystallize, filtered out and dried to obtain 1.40 g (89%) of 2HCl.H-D-Lys(ToS)-L-Phe-L-Lys-CHA.

m.p.: 191° C. (dec.).
[α]: −26.1 (Cl. MeOH).
$Rf_3$: 0.33.

EXAMPLE 2

Synthesis of H-D-Lys(ToS)-Phe-Lys PNA.2HBr (NPN-2)

I. BOC-Lys(Z)PNA (m.w. 500.557)

Under the moistureproof conditions, 56.3 g (0.148 mole) of BOC-Lys(Z)-OH (m.w. 380.444) and 20.4g (0.148 mole) of paranitroaniline (m.w. 138.13) were dissolved in 348 ml of ethyl acetate and cooled to 0° C., to which was added dropwise and gradually a solution of 15.3 g (0.074 mole) of DCC in 74 ml of ethyl acetate, then the reaction was effected at 0° C. for 2–3 hours, and then after allowing to warm to room temperature, the reaction was effected with stirring overnight.

The above reaction mixture was cooled again to 0°–5° C., a solution of 7.65 g (0.037 mole) of DCC in 37 ml of ethyl acetate was further added dropwise thereto, and the reaction was effected at 0° C. for 2–3 hours, followed by the reaction with stirring at room temperature overnight.

As the post-treatment, the DCHu was filtered off and washed with 200 ml of ether twice, then the washing was combined with the ethyl acetate layer and the mixture was washed successively with 450 ml of cold 5% HCl twice, 450 ml of $H_2O$ once, 450 ml of 5% NaH$CO_3$ twice and 450 ml of saturated aqueous NaCl twice. After drying on anhydrous $MgSO_4$ and active carbon overnight, the ethyl acetate was distilled off at 35° C. under reduced pressure to obtain 66.4 g (89.6%) of crude BOC-Lys(Z)-PNA. This was purified on Sephadex LH-20, to obtain 33.2 g (44.8%) of BOC-Lys(Z)-PNA.

m.p. 106°–109° C.
Rf 0.66 ($CHCl_3$:MeOH=9:1).

II. ESA.H-Lys(Z)-PNA (m.w. 510.6)

Under the moistureproof conditions, 75 ml of 2N ESA/acetic acid was added to 15 g (0.030 mole) of the BOC-Lys(Z)-PNA (m.w. 500.6) and the mixture was stirred at 20° C. for an hour to effect the liberation.

The reaction mixture was poured into 1.5 l of anhydrous ether, allowed to crystallize overnight then allowed to stand with cooling, after which the crystals were filtered out, washed with ethyl acetate, and dried on $P_2O_5$.KOH under reduced pressure overnight, to obtain 14.7 g (96.1%) of ESA.H-Lys(Z)-PNA.

m.p.: 100°–106° C.
$Rf_1$: 0.35.

III. BOC-Phe-Lys(Z)PNA (m.w. 647.75)

7.7 g (15 mmole) of the ESA.H-Lys(Z)PNA (m.w. 510.6) was dissolved in 19.5 ml of NEM and 38 ml of DMF and cooled to 0° C., then 6.12 g (15.75 mmole) of BOC-Phe-SDP (m.w. 387.5) was added in the powder form, after which the reaction was effected at 0°–5° C. for 2–3 hours, and after allowing to warm to room temperature, the reaction was effected with stirring overnight.

380 ml of ethyl acetate was added to the reaction mixture, which was then washed succeessively with 150 ml of cold 5% HCl twice, 150 ml of saturated aqueous NaCl once, 150 ml of 10% NaH$CO_3$ twice and 150 ml of saturated aqueous NaCl twice, anhydrous $MgSO_4$ and active carbon were added to the ethyl acetate to decolor and dry the ethyl acetate was distilled off under reduced pressure to obtain 10 g of crude crystals of BOC-Phe-Lys(Z)PNA.

The crystals were recrystallized from ethyl acetate-n-hexane to obtain 8.8 g (90.5%) of BOC-Phe-Lys(Z)-PNA.

m.p.: 157°–160° C.
Rf: 0.80 (AcOEt:n-hexane=8:2).

IV. ESA.H-Phe-Lys(Z)-PNA (m.w. 657.7)

Under the moistureproof conditions, 33.8 ml of 2N ESA/acetic acid was added to 8.7 g (13.5 mmole) of the BOC-Phe-Lys(Z)-PNA (m.w. 647.7), and the mixture was stirred at 15°–20° C. for an hour to effect the liberation.

The reaction mixture was poured into 700 ml of anhydrous ether to induce precipitation and crystallization. After allowing to stand with cooling overnight, the crystals were filtered out, washed with ethyl acetate, and dried on $P_2O_5$ KOH under reduced pressure for 2 days, to obtain 7.134 g (80.3%) of ESA.H-Phe-Lys(Z)-PNA.

m.p.: 190°–198° C.
$Rf_3$: 0.83.

V. BOC-D-Lys(ToS)-Phe-Lys(Z)PNA (m.w. 930.1)

0.599 g (1.5 mmole) of BOC-D-Lys(ToS)OH (m.w. 400.5), 0.987 g (1.5 mmole) of the ESA.H-Phe-Lys(Z)-PNA (m.w. 657.7) and 0.203 g (1.5 mmole) of HOBt were weighed respectively, and under the moistureproof conditions, they were dissolved in 6 ml of 0.5N NEM/DMF, and cooled to 0° C., after which 0.310 g (1.5 mmole) of DCC was added in the powder form, then the mixture was stirred at 0° C. for 2–3 hours, and after allowing to warm to room temperature, further stirred for the reaction overnight.

Thereafter, 60 ml of ethyl acetate was added to the reaction mixture, the precipitated PCHu was removed, the ethyl acetate layer was washed successively with 20 ml of cold 5% HCl/saturated aqueous NaCl twice, 20 ml of saturated aqueous NaCl once, 20 ml of 10% NaH$CO_3$ twice and 20 ml of saturated aqueous NaCl twice, and after drying and decoloring on anhydrous $MgSO_4$ and active carbon, the ethyl acetate was distilled off under reduced pressure, to obtain 1.1415 g (81.8%) of crude crystals of BOC-D-Lys(ToS)-Phe-Lys(Z)PNA.

Recrystallization from methanol.ethyl acetate.n-hexane gave 0.817 g (58.6%) of BOC-D-Lys(Tos)-Phe-Lys(Z)PNA.

m.p.: 165°–169.5° C.
Rf: 0.56 (AcOEt:n-hexane=7:3).

VI. H-S-Lys(Tos)-Phe-Lys(Z)PNA.2HBr (m.w. 857.7)

Under the moistureproof conditions, to 0.817 g (0.878 mmole) of the BOC-D-Lys(Tos)-Phe-Lys(Z)PNA (m.w. 930.1) while maintained at 10°–15° C. was added 35 ml of cold 25% HBr/acetic acid and the liberation was effected with stirring for an hour.

A small quantity of ethyl acetate was added to the reaction mixture to increase its volume, and the mixture was poured into 150 ml of ether, to crystallize. The crystals were filtered out, and dried on $P_2O_5$ KOH under reduced pressure to obtain 0.713 g (94.7%) of crude crystals of H-D-Lys(Tos)-Phe-Lys(Z)-PNA.2HBr. This was purified on Sephadex LH-20 to obtain 0.44 g (61.5%) of the desired product [VI].

m.p.: 148°–158° C.
Rf: 0.58.
[α]: −24.5 (C. 0.5 MeOH).

EXAMPLE 3

According to the procedures in Examples 1 and 2, the following substrates were synthesized.

| No. | Substrate | | m.p. | [α] |
|---|---|---|---|---|
| 6. | NPC-1 | H—D-Val—Leu—Lys—CHA.2HBr | 187–198° C. | −55 (C = 0.5, MeOH) |
| 7. | NPC-2 | H—D-Val—Phe—Lys—CHA.2HCl | 199–212° C. | −28 (C = 0.5, MeOH) |
| 8. | NPC-3 | H—D-Lys—Phe—Lys—CHA.3HCl | 217° C. (dec) | −25.9 (C = 1, MeOH) |
| 9. | NPC-4 | H—D-Lys(AC)—Phe—Lys—CHA.2HCl | 183–195° C. | −27 (C = 0.5, MeOH) |
| 10. | NPC-5 | H—L-Lys(Tos)—Phe—Lys—CHA.2HCl | 179–191° C. | −3 (C = 0.5, MeOH) |
| 11. | NPC-6 | H—D-Lys(Toc)—Phe—Lys—CHA.2HCl | 198–204° C. | −22 (C = 0.5, MeOH) |
| 13. | NPC-8 | H—D-Lys(NaS)—Phe—Lys—CHA.2HCl | 182–190° C. | −28 (C = 0.5, MeOH) |
| 14. | NPC-9 | H—D-Lys(NaC)—Phe—Lys—CHA.2HCl | 188–197° C. | −23 (C = 0.5, MeOH) |
| 15. | NPC-10 | H—D-Lys(Mst)—Phe—Lys—CHA.2HCl | 174–182° C. | −24 (C = 0.5, MeOH) |
| 16. | NPC-11 | H—D-Tyr(Tos)—Phe—Lys—CHA.2HCl | 183–192° C. | −28 (C = 0.5, MeOH) |
| 17. | NPC-12 | H—D-Lys(Tos)—Leu—Lys—CHA.2HBr | 169–176° C. | −43 (C = 0.5, MeOH) |
| 18. | NPC-13 | H—D-Tyr(Tos)—Leu—Lys—CHA.2HCl | 191–196° C. | −69 (C = 0.5, MeOH) |
| 3. | NPN-1 | H—D-Lys(Tos)—Leu—Lys—PNA.2HBr | 149–155° C. | −45.5 (C = 0.5, MeOH) |
| 5. | NPN-3 | H—D-Glu(CHN)—Phe—Lys—PNA.2HBr | 148–158° C. | −27.0 (C = 0.5, MeOH) |

EXAMPLE 4

The substrates produced by the above examples were used in the measurement of plasmin as follows: The principle of this measurement comprises quantitatively analyzing the decomposition product p-nitroaniline or 3-carboxy-4-hydroxyaniline produced by the enzymatic hydrolysis, by measuring the absorbance (O.D.) directly at 405 nm in the case of p-nitroaniline and, in the case of the 3-carboxy-4-hydroxyaniline at 615 nm after condensing it with 2,6-xylenol in the presence of an oxidant to develop a color.

The tables given hereinbelow compare the Km, Vmax and Vma/Km values of the plasmin substrates of the present invention and the above-described S-2251, CHZ-PL and related substrates.

The hydrolysis by an enzyme may be expressed by the following scheme:

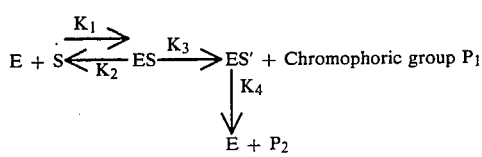

E=Enzyme
S=Substrate
ES=Enzyme-substrate complex
P$_1$ and P$_2$=Products
K$_1$, K$_2$, K$_3$ and K$_4$=Rate constants
Dissociation constant of $ES=K_2/K_1=Km$ (Michaelis's constant) where $[S]>>[E]$ and $K_4<<K_3$, the equation $$Km = \frac{[(E) - (ES)] \cdot [S]}{[ES]} \tag{1}$$

is effective.

Where P$_1$ is formed, the rate constant is as follows:

$$V = K_3 \cdot [ES] \tag{2}$$

$$V = \frac{K_3 \cdot [E] \cdot [S]}{Km + [S]}$$

Where E is completely combined to S, the following relationship holds.

$$[ES]=[E]$$

$$V = V\text{max} = K_3 \cdot [E] \tag{3}$$

Lineweaver and Burk's equation is:

$$\frac{1}{V} = \frac{Km}{V\text{max}} \cdot \frac{1}{[S]} + \frac{1}{V\text{max}} \tag{4}$$

From the equation (2), the constants Km and K$_3$ determine the efficacy of the substrate upon the given enzyme. For the measurements of these constants, the following method is adopted:

The enzyme and the substrate are mixed in a buffer solution and subjected to the hydrolysis for 30 seconds. The concentration of the substrate [S] is changed and the enzyme concentration is maintained constant. By measuring the absorbance (O.D.), the initial velocity of the hydrolysis can be determined. Where 1/V is plotted as a function of 1/[S], there is obtained a Lineweaver and Burk's linea from which graph the Vmax and Km can be determined.

The results of the measurements of the Km and Vmax along with Vmax/Km of each substrate for plasmin (pig) are summarized in Tables 1 and 2.

TABLE 1

| | | | H—A$_1$(B)—A$_2$—Lys—PNA | | |
|---|---|---|---|---|---|
| Sample No. | A$_1$ | A$_2$ | Chromophoric group | (B) | Salt |
| S-2251 | D-Val | Leu | PNA | | 2HCl |
| CHZ-PL | Gly | PrO | " | | HCl |
| NPN-1 | D-Lys | Leu | " | —SO$_2$—⟨benzene⟩—CH$_3$ | 2HBr |
| NPN-2 | D-Lys | Phe | " | —SO$_2$—⟨benzene⟩—CH$_3$ | 2HBr |
| NPN-3 | D-Glu | Phe | " | —O—⟨cyclohexyl⟩H | 2HBr |
| NPN-4 | D-Glu | Phe | " | —NH—(CH$_2$)$_2$—⟨phenyl⟩ | 2HBr |
| NPN-5 | D-Glu | Phe | " | —NH—(CH$_2$)$_3$—⟨phenyl⟩ | 2HBr |
| NPN-6 | D-Glu | Phe | " | —NH—(CH$_2$)$_4$—⟨phenyl⟩ | 2HBr |
| NPN-7 | D-Glu | Phe | " | —NH—(CH$_2$)$_2$—⟨phenyl⟩—CH$_3$ | 2HCl |

TABLE 1-continued

H—A₁(B)—A₂—Lys—PNA

| Sample No. | A₁ | A₂ | | (B) | Salt |
|---|---|---|---|---|---|
| NPN-8 | D-Glu | Phe | " | —O—(CH₂)₂—C₆H₅ | 2HBr |
| NPN-9 | D-Glu | Phe | " | —O—(CH₂)₂—C₆H₄—CH₃ | 2HBr |
| NPN-10 | D-Lys | Phe | " | —C(O)—C₆H₄—CH₃ | 2HBr |
| NPN-11 | D-Lys | Phe | " | methylnaphthalene-SO₂— | 2HBr |

| Sample No. | Km (× 10⁻⁵) | Vmax (× 10⁷) | V/Km (× 10⁻³) | Relative ratio | m.p. (°C.) | [α]_D^{20} | |
|---|---|---|---|---|---|---|---|
| S-2251 | 34.830 | 39.876 | 11.449 | 1.000 | | | |
| CHZ-PL | 27.772 | 60.067 | 21.628 | 1.889 | | | |
| NPN-1 | 18.917 | 63.600 | 33.621 | 2.937 | 149–155 | −45.5 | C = 0.5 MeOH |
| NPN-2 | 1.580 | 47.968 | 303.595 | 26.517 | 148–158 | −24.5 | C = 0.5 MeOH |
| NPN-3 | 3.217 | 65.287 | 202.943 | 17.726 | 148–158 | −27.0 | C = 0.5 MeOH |
| NPN-4 | 2.790 | 23.895 | 85.645 | 7.481 | 144–158 | −31.0 | C = 0.5 MeOH |
| NPN-5 | 3.929 | 24.892 | 63.354 | 5.534 | 148–155 | −51.0 | C = 0.5 MeOH |
| NPN-6 | 4.540 | 28.209 | 62.134 | 5.427 | 136–147 | −38.0 | C = 0.5 MeOH |
| NPN-7 | 3.937 | 20.908 | 53.106 | 4.638 | 157–167 | −22.0 | C = 0.5 MeOH |
| NPN-8 | 3.109 | 28.542 | 91.805 | 8.019 | 147–152 | −27.0 | |
| NPN-9 | 4.275 | 30.202 | 70.648 | 6.171 | 144–154 | −22.0 | C = 0.5 MeOH |
| NPN-10 | 1.551 | 26.218 | 169.039 | 14.764 | | | |
| NPN-11 | 1.790 | 23.895 | 133.491 | 11.660 | | | |

Note:
Relative ratio was obtained by dividing V/Km of each sample by that of S-2251.

TABLE 2

H—A₁(B)—A₂—Lys—CHA

| Sample No. | A₁ | A₂ | Chromophoric group | (B) | Salt |
|---|---|---|---|---|---|
| NPC-1 | D-Val | Leu | CHA | | 2HBr |
| NPC-2 | D-Val | Phe | " | | 2HCl |
| NPC-3 | D-Lys | Phe | " | | 3HCl |
| NPC-4 | D-Lys | Phe | " | —C(O)—CH₃ | 2HCl |
| NPC-5 | L-Lys | Phe | " | —SO₂—C₆H₄—CH₃ | 2HCl |
| NPC-6 | D-Lys | Phe | " | —C(O)—C₆H₄—CH₃ | 2HCl |

TABLE 2-continued

H—A₁(B)—A₂—Lys—CHA

| | | | | | |
|---|---|---|---|---|---|
| NPC-7 | D-Lys | Phe | " | —SO₂—C₆H₄—CH₃ (p-tolyl sulfonyl) | 2HCl |
| NPC-8 | D-Lys | Phe | " | 7-methyl-naphthalene-2-sulfonyl | 2HCl |
| NPC-9 | D-Lys | Phe | " | naphthalene-2-carbonyl | 2HCl |
| NPC-10 | D-Lys | Phe | " | 2,4,6-trimethylphenylsulfonyl | 2HCl |
| NPC-11 | D-Tyr | Phe | " | —SO₂—C₆H₄—CH₃ | 2HCl |
| NPC-12 | D-Lys | Leu | " | —SO₂—C₆H₄—CH₃ | 2HBr |
| NPC-13 | D-Tyr | Leu | " | —SO₂—C₆H₄—CH₃ | 2HCl |
| NPC-14 | D-Lys | Phe | " | —C(O)—C₆H₅ | 2HCl |
| NPC-15 | D-Lys | Phe | " | —SO₂—C₆H₅ | 2HCl |
| NPC-16 | D-Lys | Phe | " | —C(O)—CH₂—C₆H₅ | 2HCl |
| NPC-17 | D-Lys | Phe | " | naphthalene-1-sulfonyl | 2HCl |
| NPC-18 | D-Orn | Phe | " | —SO₂—C₆H₄—CH₃ | 2HCl |
| NPC-19 | D-Lys | Phe | " | —C(O)—CH₂CH₂CH₃ | 2HCl |

TABLE 2-continued

H—A₁(B)—A₂—Lys—CHA

| Sample | A₁ | A₂ | | R | Salt |
|---|---|---|---|---|---|
| NPC-20 | D-Lys | Phe | " | —Z | 2HCl |
| NPC-21 | D-Asp | Phe | " | —O—CH(CH₃)₂ | 2HCl |
| NPC-22 | D-Asp | Phe | " | —O—C₆H₁₁ | 2HCl |
| NPC-23 | D-Glu | Phe | " | —NH—CH₂CH₂—C₆H₅ | 2HCl |
| NPC-24 | D-Glu | Phe | " | —NH—CH₂CH₂—C₆H₄—CH₃ | 2HCl |
| NPC-25 | D-Lys | Phe | " | —SO₂—CH₃ | 2HCl |

| Sample No. | Km (× 10⁻⁵) | Vmax (× 10⁻⁷) | V/Km (× 10⁻³) | Relative ratio | m.p. (°C.) | | $[\alpha]_D^{20}$ |
|---|---|---|---|---|---|---|---|
| NPC-1 | 321.027 | 3.556 | 0.111 | 1.000 | 187–198 | −55 | C = 0.5 MeOH |
| NPC-2 | 63.066 | 8.266 | 1.311 | 11.811 | 199–212 | −28 | C = 0.5 MeOH |
| NPC-3 | 22.222 | 7.506 | 3.378 | 30.432 | 217(dec.) | −25.9 | C = 1 MeOH |
| NPC-4 | 25.043 | 10.940 | 4.368 | 39.351 | 183–195 | −27 | C = 0.5 MeOH |
| NPC-5 | 29.232 | 3.159 | 1.081 | 9.739 | 179–191 | −3 | C = 0.5 MeOH |
| NPC-6 | 7.620 | 11.670 | 15.315 | 137.973 | 198–204 | −22 | C = 0.5 MeOH |
| NPC-7 | 20.629 | 29.417 | 14.260 | 128.468 | 191(dec.) | −26.1 | C = 0.5 MeOH |
| NPC-8 | 17.939 | 30.814 | 17.177 | 154.748 | 182–190 | −28 | C = 0.5 MeOH |
| NPC-9 | 32.546 | 13.827 | 4.248 | 38.270 | 188–197 | −23 | C = 0.5 MeOH |
| NPC-10 | 27.155 | 28.445 | 10.475 | 94.369 | 174–182 | −24 | C = 0.5 MeOH |
| NPC-11 | 15.404 | 17.018 | 11.048 | 99.532 | 183–192 | −28 | C = 0.5 MeOH |
| NPC-12 | 100.000 | 25.679 | 2.568 | 23.135 | 169–176 | −43 | C = 0.5 MeOH |
| NPC-13 | 144.340 | 17.991 | 1.246 | 11.225 | 191–196 | −69 | C = 0.5 MeOH |
| NPC-14 | 33.444 | 33.794 | 10.105 | 91.036 | 174–191 | −27 | C = 0.5 MeOH |
| NPC-15 | 53.236 | 37.927 | 7.124 | 64.180 | 165–182 | −29 | C = 0.5 MeOH |
| NPC-16 | 35.666 | 26.986 | 7.566 | 68.162 | 160–178 | −26 | C = 0.5 MeOH |
| NPC-17 | 59.637 | 15.803 | 2.650 | 23.874 | 185(dec.) | | — |
| NPC-18 | 54.233 | 35.252 | 6.500 | 58.558 | 173–195 | −32 | C = 0.5 MeOH |
| NPC-19 | 23.930 | 8.266 | 3.454 | 31.117 | 208(dec.) | | — |
| NPC-20 | 49.553 | 40.725 | 8.218 | 74.040 | 157–170 | −49 | C = 0.5 MeOH |
| NPC-21 | 35.185 | 6.802 | 1.933 | 17.414 | 160–176 | −59 | C = 0.5 MeOH |
| NPC-22 | 37.945 | 17.991 | 4.741 | 42.715 | 194–201 | −52 | C = 0.5 MeOH |
| NPC-23 | 39.689 | 18.963 | 4.778 | 43.045 | 157–167 | −60 | C = 0.5 MeOH |
| NPC-24 | 41.700 | 21.637 | 5.189 | 46.748 | 160–172 | −52 | C = 0.5 MeOH |
| NPC-25 | 32.643 | 15.803 | 4.841 | 43.613 | 193(dec.) | −29 | C = 0.5 MeOH |

Note: Relative ratio was obtained by dividing V/Km of each sample by that of S-2251.

EXAMPLE 5

The specificities of the novelly synthesized substrates were tested by reacting them with various enzymes respectively.

Testing Method (1) Substrate solution concentration: 35 mmole/liter $H_2O$ (2) Buffer: Tris-hydrochloric acid buffer 50 mmole/l, NaCl 150 mmole/l (0.875%) was employed, and the pH for reaction was as follows depending on the enzyme.

| Enzyme | pH (25° C.) |
|---|---|
| Thrombin (TH) | 8.4 |
| Plasmin (PL) | 7.4 |
| Kallikrein (KL) | 7.9 |
| Factor-Xa (FXa) | 8.4 |
| Urokinase (UK) | 8.2 |

(3) Enzymes Used

| | Origin | Manufacturer | Lot No. | Units |
|---|---|---|---|---|
| Thrombin | Cow | Mochida* (Japan) | OA 411 | 1.0 NIH/ml |
| Plasmin | Pig | Sigma (U.S.A.) | 118c-02841 | 0.32 CU/ml |
| Kallikrein | Pig | Sigma (U.S.A.) | 118c-0214 | 1.0 BAEE-U/ml |
| F-Xa | Cow | Sigma (U.S.A.) | 60 F-3953 | 0.4 U/ml |
| Urokinase | Human | Mochida* (Japan) | A-131 | 1000 IU/ml |

*Mochida Pharmaceutical Co., Ltd.

(4) Reaction terminating solution (PNA)
10% Acetic acid (5) Color developing reagent
2,6-Xylenol 7.0 mmole + $NaIO_4$ 1.5 mmole/0.2N KOH

Measuring Method 0.5 ml of the buffer solution and 0.05 ml of the enzyme reagent were taken into a silicon-treated hard glass test tube or a plastic test tube, and preheated in a constant temperature bath at 37° C. for 5 minutes. Thereafter, 0.1 ml of the substrate solution was added to effect the enzymatic reaction at 37° C. for 10 minutes. Exactly after 10 minutes, 2.5 ml of the reaction terminating solution or the terminating and color developing reagent solution was added to terminate the enzymatic reaction, and after allowing to stand at 25° C. for 10 minutes, the absorbance at 405 nm or 645 nm was measured, in which

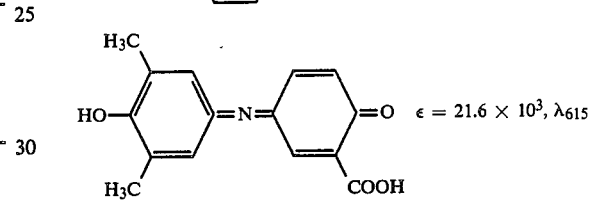

TABLE 3

$H-A_1(B)-A_2-Lys-PNA$

| Sample No. | $A_1$ | $A_2$ | Chromophoric group | (B) | Salt | Selectivity TH | PL | KL | FXa | UK |
|---|---|---|---|---|---|---|---|---|---|---|
| S-2251 | D-Val | Leu | PNA | | 2HCl | 0.001 | 0.306 | 0.017 | 0.007 | 0.001 |
| CHz-PL | Gly | Pro | " | | HCl | 0.057 | 0.647 | 0.004 | 0.026 | 0.069 |
| NPN-1 | D-Lys | Leu | " | $-SO_2-\phi-CH_3$ | 2HBr | 0 | 0.457 | 0.006 | 0.003 | 0.001 |
| NPN-2 | D-Lys | Phe | " | $-SO_2-\phi-CH_3$ | 2HBr | 0 | 0.383 | 0.004 | 0.003 | 0.001 |
| NPN-3 | D-Glu | Phe | " | $-O-C_6H_{11}$ | 2HBr | 0 | 0.466 | 0.009 | 0.003 | 0.001 |
| NPN-4 | D-Glu | Phe | " | $-NH-(CH_2)_2-\phi$ | 2HBr | 0.001 | 0.330 | 0.010 | 0.006 | 0.002 |
| NPN-5 | D-Glu | Phe | " | $-NH-(CH_2)_3-\phi$ | 2HBr | 0 | 0.525 | 0.014 | 0.005 | 0.001 |

TABLE 3-continued

H—A₁(B)—A₂—Lys—PNA

| Sample No. | A₁ | A₂ | Chromophoric group | (B) | Salt | Selectivity | | | | |
|---|---|---|---|---|---|---|---|---|---|---|
| | | | | | | TH | PL | KL | FXa | UK |
| NPN-6 | D-Glu | Phe | " | —NH—(CH₂)₄—C₆H₅ | 2HBr | 0 | 0.646 | 0.018 | 0.003 | 0.012 |
| NPN-7 | D-Glu | Phe | " | —NH—(CH₂)₂—C₆H₄—CH₃ | 2HCl | 0.001 | 0.427 | 0.011 | 0.008 | 0.002 |
| NPN-8 | D-Glu | Phe | " | —O—(CH₂)₂—C₆H₅ | 2HBr | 0 | 0.181 | 0.014 | 0.005 | 0.003 |
| NPN-9 | D-Glu | Phe | " | —O—(CH₂)₂—C₆H₄—CH₃ | 2HBr | 0 | 0.299 | 0.016 | 0.006 | 0.002 |
| NPN-10 | D-Lys | Phe | " | —C(O)—C₆H₄—CH₃ | 2HBr | 0.001 | 0.335 | 0.011 | 0.006 | 0.001 |
| NPN-11 | D-Lye | Phe | " | naphthyl-SO₂— | 2HBr | 0 | 0.171 | 0.001 | 0.005 | 0.001 |

Note:
Initial substrate concentration $S_o$ = 0.54 mmole/l
The measured values indicate the absorbances (O.D.) measured at 405 nm.

TABLE 4

H—A₁(B)—A₂—Lys—CHA

| Sample No. | A₁ | A₂ | Chromophoric group | (B) | Salt | Selectivity | | | | |
|---|---|---|---|---|---|---|---|---|---|---|
| | | | | | | TH | PL | KL | FXa | UK |
| NPC-1 | D-Val | Leu | CHA | | 2HBr | 0 | 0.013 | 0.002 | 0.002 | 0 |
| NPC-2 | D-Val | Phe | " | | 2HCl | 0.002 | 0.090 | 0.006 | 0.004 | 0.002 |
| NPC-3 | D-Lys | Phe | " | | 3HCl | 0 | 0.096 | 0.004 | 0.002 | 0 |
| NPC-4 | D-Lys | Phe | " | —C(O)—CH₃ | 2HCl | 0.001 | 0.144 | 0.006 | 0.002 | 0 |
| NPC-5 | L-Lys | Phe | " | —SO₂—C₆H₄—CH₃ | 2HCl | 0 | 0.051 | 0.001 | 0.002 | 0 |
| NPC-6 | D-Lys | Phe | " | —C(O)—C₆H₄—CH₃ | 2HCl | 0 | 0.147 | 0.007 | 0.001 | 0 |
| NPC-7 | D-Lys | Phe | " | —SO₂—C₆H₄—CH₃ | 2HCl | 0 | 0.420 | 0.007 | 0.001 | 0 |
| NPC-8 | D-Lys | Phe | " | naphthyl-SO₂— | 2HCl | 0 | 0.498 | 0.011 | 0.002 | 0.002 |

TABLE 4-continued

H—A₁(B)—A₂—Lys—CHA

| Sample No. | A₁ | A₂ | Chromophoric group | (B) | Salt | Selectivity TH | PL | KL | FXa | UK |
|---|---|---|---|---|---|---|---|---|---|---|
| NPC-9 | D-Lys | Phe | " | naphthalene-2-C(=O)— | 2HCl | 0 | 0.120 | 0.027 | 0.001 | 0 |
| NPC-10 | D-Lys | Phe | " | 2,4,6-trimethylphenyl-SO₂— | 2HCl | 0 | 0.344 | 0.010 | 0.002 | 0.001 |
| NPC-11 | D-Tyr | Phe | " | 4-CH₃-C₆H₄-SO₂— | 2HCl | 0.001 | 0.277 | 0.012 | 0.003 | 0.003 |
| NPC-12 | D-Lys | Leu | " | 4-CH₃-C₆H₄-SO₂— | 2HBr | 0.001 | 0.051 | 0.007 | 0.002 | 0.001 |
| NPC-13 | D-Tyr | Leu | " | 4-CH₃-C₆H₄-SO₂— | 2HCl | 0.002 | 0.041 | 0.004 | 0.001 | 0.001 |
| NPC-14 | D-Lys | Phe | " | C₆H₅-C(=O)— | 2HCl | 0 | 0.417 | 0.016 | 0.002 | 0.001 |
| NPC-15 | D-Lys | Phe | " | C₆H₅-SO₂— | 2HCl | 0 | 0.480 | 0.010 | 0.002 | 0 |
| NPC-16 | D-Lys | Phe | " | C₆H₅-CH₂-C(=O)— | 2HCl | 0 | 0.325 | 0.012 | 0.002 | 0.001 |
| NPC-17 | D-Lys | Phe | " | naphthalene-1-SO₂— | 2HCl | 0 | 0.192 | 0.002 | 0 | 0 |
| NPC-18 | D-Orn | Phe | " | 4-CH₃-C₆H₄-SO₂— | 2HCl | 0 | 0.392 | 0.019 | 0.002 | 0.001 |
| NPC-19 | D-Lys | Phe | " | —C(=O)—CH₂CH₂CH₃ | 2HCl | 0.001 | 0.118 | 0.004 | 0.002 | 0.001 |
| NPC-20 | D-Lys | Phe | " | —Z | 2HCl | 0 | 0.467 | 0.019 | 0.006 | 0.004 |
| NPC-21 | D-Asp | Phe | " | —O—CH(CH₃)₂ | 2HCl | 0 | 0.093 | 0.010 | 0.003 | 0.004 |

TABLE 4-continued

H—A₁(B)—A₂—Lys—CHA

| Sample No. | A₁ | A₂ | Chromophoric group | (B) | Salt | Selectivity | | | | |
|---|---|---|---|---|---|---|---|---|---|---|
| | | | | | | TH | PL | KL | FXa | UK |
| NPC-22 | D-Asp | Phe | " | 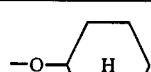 | 2HCl | 0 | 0.213 | 0.023 | 0.015 | 0.026 |
| NPC-23 | D-Glu | Phe | " |  | 2HCl | 0 | 0.223 | 0.009 | 0.005 | 0.004 |
| NPC-24 | D-Glu | Phe | " |  | 2HCl | 0 | 0.279 | 0.009 | 0.005 | 0.004 |
| NPC-25 | D-Lys | Phe | " | —SO₂—CH₃ | 2HCl | 0 | 0.185 | 0.006 | 0 | 0 |

Note:
Initial substrate concentration $S_o$ = 0.54 mmole/l
The measured values indicate the absorbances (O.D.) measured at 645 nm.

What is claimed is:

1. A method for measuring the activity of plasmin in plasma which comprises reacting a compound of the following formula or a salt thereof:

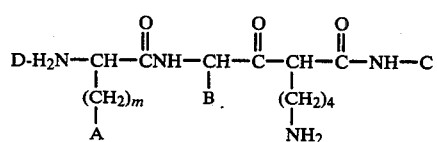

wherein
m = 1, 2, 3 or 4

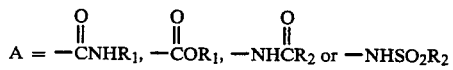
$A = -\overset{O}{\underset{\|}{C}}NHR_1, -\overset{O}{\underset{\|}{C}}OR_1, -NH\overset{O}{\underset{\|}{C}}R_2 \text{ or } -NHSO_2R_2$

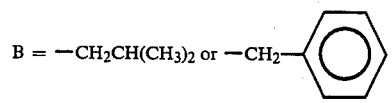
$B = -CH_2CH(CH_3)_2 \text{ or } -CH_2-\bigcirc$

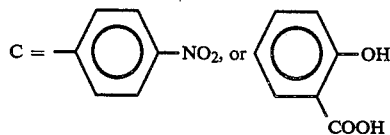
$C = -\bigcirc-NO_2, \text{ or } -\bigcirc-OH, -COOH$ wherein

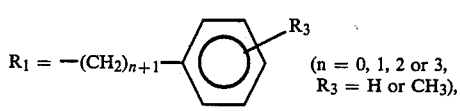
$R_1 = -(CH_2)_{n+1}-\bigcirc^{R_3}$ (n = 0, 1, 2 or 3, R₃ = H or CH₃), —(CH₂)ₙ—CH(CH₃)₂ (n = 0, 1, 2 or 3)

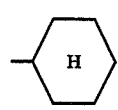

$R_2 = -(CH_2)_{n+1}-CH_3$ (n = 0, 1, 2 or 3)

-continued

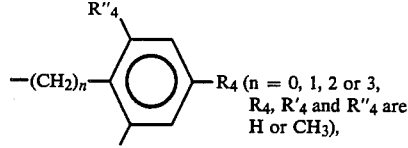
$-(CH_2)_n-\bigcirc^{R''_4}_{R'_4}-R_4$ (n = 0, 1, 2 or 3, R₄, R'₄ and R''₄ are H or CH₃),

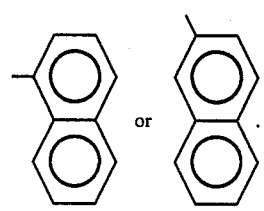

with plasmin in a buffer solution having a pH of 7.2 to 7.6 and quantitatively determining the reaction product thereof.

2. A method for measuring the activity of plasmin in plasma which comprises (a) reacting a compound of the following formula or a salt thereof:

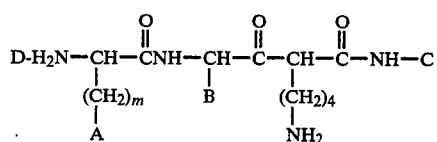

wherein
m = 1, 2, 3 or 4

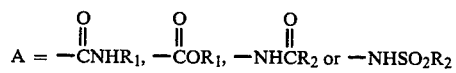
$A = -\overset{O}{\underset{\|}{C}}NHR_1, -\overset{O}{\underset{\|}{C}}OR_1, -NH\overset{O}{\underset{\|}{C}}R_2 \text{ or } -NHSO_2R_2$

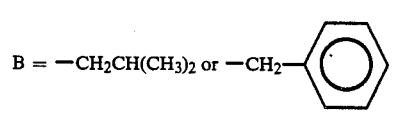
$B = -CH_2CH(CH_3)_2 \text{ or } -CH_2-\bigcirc$

-continued
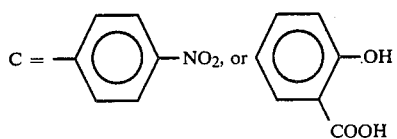
wherein
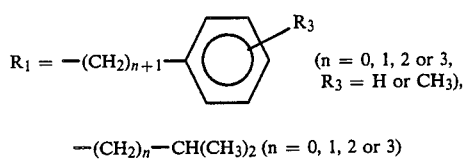
$-(CH_2)_n-CH(CH_3)_2$ (n = 0, 1, 2 or 3)
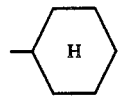
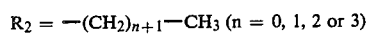
$R_2 = -(CH_2)_{n+1}-CH_3$ (n = 0, 1, 2 or 3)
-continued
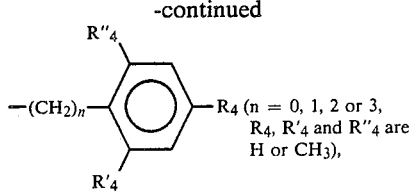
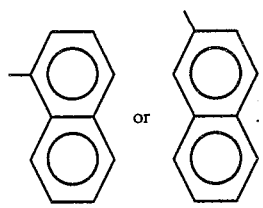
with plasmin in a buffer solution having a pH of 7.2 to 7.6; (b) oxidatively condensing the reaction product of step (a) with a coupler to convert to a colored compound; and (c) quantitatively determining the compound by colorimetry.
* * * * *